United States Patent
Brillouet et al.

(10) Patent No.: US 10,130,578 B2
(45) Date of Patent: Nov. 20, 2018

(54) TOPICAL DELIVERY OF SKIN COMPOSITIONS HAVING LOW PH

(71) Applicant: Johnson & Johnson Consumer Inc., Skillman, NJ (US)

(72) Inventors: Anne-Sophie Brillouet, Pennington, NJ (US); Marisa DeVita Dufort, Hillsborough, NJ (US); Ali Fassih, Franklin Park, NJ (US); Devin L. Garcia, Middlesex, NJ (US); Ya-Ping Hu, Somerset, NJ (US); Wen-Hwa Ting Li, Cranbury, NJ (US); Ramine Parsa, Lawrenceville, NJ (US); Jyotsna Paturi, Skillman, NJ (US); Dianne Rossetti, Branchburg, NJ (US); Ying Sun, Belle Mead, NJ (US); Janet Wangari-Talbot, Hillsborough, NJ (US); Robert Wayne Yates, Warminster, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 14/806,699

(22) Filed: Jul. 23, 2015

(65) Prior Publication Data
US 2017/0020799 A1   Jan. 26, 2017

(51) Int. Cl.
| A61K 8/73 | (2006.01) |
| A61K 8/37 | (2006.01) |
| A61K 8/26 | (2006.01) |
| A61K 8/81 | (2006.01) |
| A61K 8/365 | (2006.01) |
| A61K 8/34 | (2006.01) |
| A61Q 19/00 | (2006.01) |
| A61K 8/36 | (2006.01) |
| A61K 8/39 | (2006.01) |

(52) U.S. Cl.
CPC .......... *A61K 8/735* (2013.01); *A61K 8/26* (2013.01); *A61K 8/345* (2013.01); *A61K 8/36* (2013.01); *A61K 8/365* (2013.01); *A61K 8/375* (2013.01); *A61K 8/39* (2013.01); *A61K 8/8152* (2013.01); *A61Q 19/00* (2013.01); *A61Q 19/007* (2013.01); *A61K 2800/48* (2013.01); *A61K 2800/592* (2013.01)

(58) Field of Classification Search
CPC ........ A61K 8/735; A61K 8/365; A61K 8/375; A61K 8/345; A61K 8/8152; A61K 8/26; A61K 2800/48; A61K 2800/592; A61Q 19/007
USPC ...................................................... 514/474
See application file for complete search history.

(56) References Cited

U.S. PATENT DOCUMENTS

| 4,636,524 A | 1/1987 | Balazs et al. |
| 5,399,351 A | 3/1995 | Leshchiner et al. |
| 6,284,234 B1 | 9/2001 | Niemiec et al. |
| 6,419,913 B1 | 7/2002 | Niemiec et al. |
| 7,385,052 B2 | 6/2008 | Zhao |
| 7,514,541 B2 | 4/2009 | Zhao |
| 7,521,434 B2 | 4/2009 | Leshchiner et al. |
| 7,741,476 B2 | 6/2010 | Lebreton |
| 8,080,641 B2 | 12/2011 | Zhao |
| 8,247,390 B2 | 8/2012 | Leshchiner et al. |
| 8,338,388 B2 | 12/2012 | Lebreton |
| 8,481,080 B2 | 7/2013 | Longin et al. |
| 8,524,213 B2 | 9/2013 | Leshchiner et al. |
| 2005/0019282 A1 | 1/2005 | Rendon |
| 2007/0036745 A1 | 2/2007 | Leshchiner et al. |
| 2008/0003271 A1 | 1/2008 | Abdellaoui et al. |
| 2008/0057091 A1 | 3/2008 | Abdellaoui et al. |
| 2010/0135935 A1 | 6/2010 | Leshchiner et al. |
| 2010/0255068 A1 | 10/2010 | Stroumpoulis et al. |
| 2012/0014885 A1* | 1/2012 | Collier .................... A61K 8/64 424/59 |
| 2012/0258155 A1 | 10/2012 | Wenk et al. |
| 2014/0256833 A1 | 9/2014 | Gunn et al. |
| 2015/0126618 A1 | 5/2015 | Pollock |

FOREIGN PATENT DOCUMENTS

| EP | 0224987 B1 | 4/1992 |
| JP | S63211210 A | 9/1988 |
| WO | WO 02/15860 A1 | 2/2002 |
| WO | WO 03/089476 A1 | 10/2003 |
| WO | WO 2008/031194 | 3/2008 |
| WO | WO 2012/064766 A2 | 5/2012 |

OTHER PUBLICATIONS

HyaCare® Filler CL, Press release, Evonik Industries AG, Dr. Hans-Georg Kreul Consumer Specialties Public Relations. May 18, 2010.*
Glycolactic® Complex Products—ABBELabs—Private Label Skin Care ManufacturerABBELabs—Private Label Skin Care Manufacturer. 2011. http://pro.abbelabs.com/glycolactic®-complex-products/ (Year: 2011).*
"HyaCare® Filler CL Product Data Record", Evonik Industries, Edition 15, May 8, 2013.
"HyaCare® Filler CL The Topical Wrinkle Smoother", Evonik Industries, Apr. 2008.
Database GNPD [online] Mintel; Jun. 2015 (Jun. 2015), "Mango and Exotic Fruit Ice Tea", XP002761337, Database Accession No. 3222675, p. 2.
Database GNPD [online] Mintel; Jan. 2009 (Jan. 2009), "Snail Extract Cream", XP002761338, Database Accession No. 1034065, product description; p. 1, p. 2.

(Continued)

*Primary Examiner* — Yih-Horng Shiao

(57) ABSTRACT

Low pH compositions for topical administration to skin are provided. They comprise a buffering agent having a pKa of about 2.8 to about 4.2 and a cosmetically acceptable active ingredient having a pKa within about 1 unit of the pKa of the buffering agent. The composition has a pH of about 3.3 to 4 and a buffer capacity of at least about 0.15. A method of increasing the topical delivery of a cosmetically acceptable active ingredient having a pKa of about 2.8 to about 4 is also provided.

18 Claims, No Drawings

(56) References Cited

OTHER PUBLICATIONS

JP S63 211210A (Sunstar Inc.) Sep. 2, 1988 (Sep. 2, 1988) Abstract & Database WPI Week 198841, Thomson Scientific, London, GB; AN 1988-289034 & JP S63 211210 A (Sunstar KK) Sep. 2, 1988 (Sep. 2, 1988), Abstract.
European Search Report for corresponding application No. EP 16 18 0841 dated Sep. 1, 2016.
Pavicic et al., "Efficacy of cream-based novel formulations of hyaluronic acid of different molecular weights in anti-wrinkle treatment", *Journal of Drugs in Dermato, Strategic Communication in Dermatology*, New York, NY, US, vol. 10, No. 9, Sep. 1, 2011, pp. 990-1000, XP008146386, ISSN 1545-9616.
Berko et al., "Advantages of cross-linied versus linear hyaluronic acid for semisolid skin delivery systems", European Polymer Journal, vol. 49, No. 9, pp. 2511-2517, XP028689528, ISSN 0014-3057, DOI 10.1016/J.EURPOLYMJ.2013.04.001.

\* cited by examiner

TOPICAL DELIVERY OF SKIN COMPOSITIONS HAVING LOW PH

FIELD OF THE INVENTION

The present invention relates to low pH compositions for topical administration to skin. They comprise a buffering agent having a pKa of about 2.8 to about 4.2 and a cosmetically acceptable active ingredient having a pKa within about 1 unit of the pKa of the buffering agent. The composition has a pH of about 3.3 to about 4 and a buffer capacity of at least about 0.15. A method of increasing the topical delivery of a cosmetically acceptable active ingredient having a pKa of about 2.8 to about 4 is also provided.

BACKGROUND OF THE INVENTION

Hyaluronic acid or hyaluronan (HA) is a naturally occurring high molecular weight polysaccharide that consists of alternating N-acetyl-D-glucosamine and D-glucuronic acid monosaccharide units linked with alternating [beta] 1-3 glucoronidic and [beta] 1-4 glucosaminidic bonds. It is a commonly occurring glycosaminoglycan (GAG) in the body. The molecular weight of linear hyaluronic acid is generally within the range of 50,000 to 8,000,000 or more. Hyaluronic acid is present in cartilage, joint fluids, and skin tissue. It is plays a role in several biological processes in the body, such as moisturization and lubrication of tissues, and is used to treat joint disorders, promote wound healing and the formation of vessels.

Hyaluronic acid has also been widely employed in the treatment of skin. Commercially available cosmetic compositions often contain linear hyaluronic acid as a moisturizing agent. However, the utility of linear hyaluronic acid is sometimes limited by the fact that it is rapidly degraded by hyaluronidase in the body.

Cross-linked hyaluronic acid provides improved mechanical properties and in vivo residence time. For example, HyaCare® Filler CL, commercially available from Evonik Industries AG, is a wrinkle smoother comprising a water-in-oil emulsion containing small particles of cross-linked hyaluronic acid in a vehicle of water, ethylhexyl stearate, polyglyceryl-4 diisostearate/polyhydroxystearate/sebacate, and sodium isostearate. Hylasome® EG10, sold by Vantage Specialty Ingredients, is another example of commercially available cross-linked hyaluronic acid for skin care use.

Hyaluronic acid is also used commercially as injectable filler to address wrinkles and other signs of skin aging. However, injections are typically painful, particularly in the face, and must be administered by a medical professional. It would be desirable to deliver hyaluronic acid, particularly cross-linked hyaluronic acid, and other large, cosmetically acceptable active ingredients by topical administration, which is convenient and painless. However, the stratum corneum of mammalian skin presents a formidable barrier to the penetration. The ability of a substance applied to the skin surface to penetrate through the skin is inversely related to the thickness of the stratum corneum layer. In addition, permeation of cross-linked hyaluronic acid and other large molecules into the skin is made more difficult because of their size. The large polymeric structure that gives hyaluronic acid its beneficial effects also makes it difficult to administer topically.

Compositions and methods for the topical delivery of hyaluronic acid, including cross-linked hyaluronic acid, and other large molecules have now been identified. Specifically, the present inventors have found that low pH topical compositions containing a buffering agent having a pKa of about 2.8 to about 4.2 and providing a buffering capacity of at least 0.15 provide increased penetration of hyaluronic acid and other large cosmetically acceptable active ingredients having pKa's of about 2.8 to about 4 into mammalian skin. Methods of increasing the topical delivery of such cosmetically acceptable active ingredients are also provided.

SUMMARY OF THE INVENTION

The present invention provides a topical composition comprising: (a) a buffering agent having a pKa of about 2.8 to about 4.2; and (b) a cosmetically acceptable active ingredient having a pKa within about 1 unit of the pKa of the buffering agent; wherein the composition has a pH of about 3.3 to about 4 and a buffer capacity of at least about 0.15.

The present invention also provides a topical composition comprising: (a) hyaluronic acid; (b) lactic acid; (c) steareth 10; (d) glycerol dilaurate; and (e) glycerin.

The present invention further provides a method of increasing the topical delivery of a cosmetically acceptable active ingredient having a pKa of about 2.8 to about 4, comprising topically administering the cosmetically acceptable active ingredient in a composition having a pH of about 3.3 to about 4, a buffer capacity of at least about 0.15, and containing a buffering agent having a pKa of about 2.8 to about 4.2.

The present invention also provides a topical composition comprising: (a) lactic acid; (b) steareth 10; (c) glycerol dilaurate; and (d) glycerin.

DETAILED DESCRIPTION OF THE INVENTION

Unless defined otherwise, all technical and scientific terms used herein have the same meaning as commonly understood by one of ordinary skill in the art to which the invention belongs. All publications, patent applications, patents, and other references mentioned herein are incorporated by reference.

The term "buffer capacity" is a well-known chemical term, defined as the moles of an acid or base necessary to change the pH of a solution by 1, divided by the pH change and the volume of buffer in liters. It is a unitless number. A buffer resists changes in pH due to the addition of an acid or base though consumption of the buffer.

As used herein, "topically applying" means directly laying on or spreading on outer skin, the scalp, or hair, e.g., by use of the hands or an applicator such as a wipe, roller, or spray.

As used herein, "cosmetically acceptable" means that the ingredients the term describes are suitable for use in contact with tissues (e.g., the skin or hair) without undue toxicity, incompatibility, instability, irritation, allergic response, or the like.

As used herein, a "cosmetically acceptable active agent" is a compound (e.g., a synthetic compound or a compound isolated from a natural source or a natural extract) that has a cosmetic or therapeutic effect on the skin or hair, including, but not limited to, anti-acne agents, shine control agents, anti-microbial agents, anti-inflammatory agents, anti-mycotic agents, anti-parasite agents, external analgesics, sunscreens, photoprotectors, antioxidants, keratolytic agents, surfactants, moisturizers, nutrients, vitamins, energy enhancers, anti-perspiration agents, astringents, deodorants, firming agents, anti-callous agents, and agents for hair and/or skin conditioning.

Compositions of the present invention are suitable for treating signs of skin aging. As used herein, "signs of skin aging" includes the presence of lines and wrinkles, loss of elasticity, uneven skin, and blotchiness. In a particularly preferred embodiment, the sign of aging is the presence of lines and wrinkles and/or loss of elasticity.

As used herein, "treating signs of skin aging" refers to mitigating, reducing, preventing, improving, or eliminating the presence or signs of skin aging described above.

As used herein, "wrinkle" includes fine lines, fine wrinkles, or coarse wrinkles. Examples of wrinkles include, but are not limited to, fine lines around the eyes (e.g., "crow's feet"), forehead and cheek wrinkles, frown-lines, and laugh-lines around the mouth.

As used herein, "loss of elasticity" includes loss of elasticity or structural integrity of the skin or tissue, including but not limited to sagging, lax and loose tissue. The loss of elasticity or tissue structure integrity may be a result of a number of factors, including but not limited to disease, aging, hormonal changes, mechanical trauma, environmental damage, or the result of an application of products, such as a cosmetics or pharmaceuticals, to the tissue.

As used herein, "uneven skin" means a condition of the skin associated with diffuse or mottled pigmentation, which may be classified as hyperpigmentation, such as post-inflammatory hyperpigmentation.

As used herein, "blotchiness" means a condition of the skin associated with redness or erythema.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "cosmetically effective amount" means an amount of a physiologically active compound or composition sufficient for treating one or more signs of skin aging, but low enough to avoid serious side effects. The cosmetically effective amount of the compound or composition will vary with the particular condition being treated, the age and physical condition of the end user, the severity of the condition being treated/prevented, the duration of the treatment, the nature of other treatments, the specific compound or product/composition employed, the particular cosmetically-acceptable carrier utilized, and like factors.

Compositions of the invention are also useful for treating skin in need of moisturization. As used herein, "skin in need of moisturization" means a skin that is, but not limited to, lacking in moisture, lacking in sebum, cracked, dry, itchy, scaly, xerodermic, dehydrated, lacks suppleness, lacks radiance, dull, or lacks lipids.

Unless otherwise indicated, a percentage or concentration refers to a percentage or concentration by weight (i.e., % (W/W). Unless stated otherwise, all ranges are inclusive of the endpoints, e.g., "from 4 to 9" includes the endpoints 4 and 9.

The composition of the invention comprises: (a) a buffering agent having a pKa of about 2.8 to about 4.2, and (b) a cosmetically acceptable active ingredient having a pKa within about one unit of the pKa of the buffering agent.

The pH of the composition is preferably from about 3 to about 4. Preferably, the pH of the composition is from about 3.1 to about 3.5.

Cosmetically Acceptable Active Ingredient

The cosmetically acceptable active ingredient has a pKa of within about one unit of the pKa of the buffering agent used. In one embodiment, the cosmetically acceptable active ingredient has a pKa of within about 0.7 unit of the pKa of the buffering agent.

In one embodiment, the cosmetically acceptable active ingredient is selected from glycosaminoglycans, peptides, amino acids, starches, sugars and other cosmetically acceptable active agents having a pKa in the range of about 2.8 to about 4.

Preferably, the cosmetically acceptable active ingredient comprises a glycosaminoglycan.

For example, the cosmetically acceptable active ingredient may comprise hyaluronic acid. The hyaluronic acid may be linear, cross-linked, or a mixture of linear and cross-linked hyaluronic acid. The molecular weight of the hyaluronic acid may vary as desired from very low molecular weight to very high molecular weight.

In one particular embodiment the cosmetically acceptable active ingredient is or comprises cross-linked hyaluronic acid.

In another embodiment, the cosmetically acceptable active ingredient comprises a mixture of linear and cross-linked hyaluronic acid.

Hyaluronic acid has a pKa of 2.9.

A commercially available cross-linked hyaluronic acid useful in the present invention is HyaCare® Filler CL from Evonik Industries AG. HyaCare® Filler CL is a fermentation-derived high-quality biopolysaccharide of high purity which is obtained by a solvent-free process. It is skin-identical hyaluronic acid with a medium molecular weight of 700 kDa.

Another commercially available cross-linked hyaluronic acid useful in the present invention is Hylasome® EG10, sold by Vantage Specialty Ingredients.

The cross-linked hyaluronic acid may be prepared as known in the art. For example, natural or synthetic sources of linear hyaluronic acid may be cross-linked with a variety of cross-linkers, including divinyl sulfone (DVS), formaldehyde, polyanhydrides, polyaldehydes, polyhydric alcohols, carbodiimides, epichlorohydrin, ethylene glycol diglycidylether, butanediol diglycidylether, polyglycerol polyglycidylether, polyethylene glycol, polypropylene glycol diglycidylether, bis- or poly-epoxy cross-linkers such as 1,2,3,4-diepoxybutane or 1,2,7,8-diepoxyoctane, or other cross-linkers known in the art. The degree of cross-linking may be adjusted also as known in the art.

Buffering Agent and Buffer Capacity

The buffering agent has a pKa of about 2.8 to about 4.2, preferably about 3.5 to about 4.

The buffering agent may for example be lactic acid, glycolic acid, citric acid, malic acid, tartaric acid, gluconic acid, or gluconolactone. Preferably the buffering agent is lactic acid.

The amount of buffering agent in the composition is suitable to provide the composition with a buffer capacity greater than about 0.15, or greater than about 0.17, or greater than about 0.25.

Typically, the composition contains about 3 to about 12, or about 4 to about 8, weight percent of buffering agent.

Emulsions

In one embodiment, the composition is an emulsion comprising an aqueous phase, oil phase, and non-ionic lipid phase.

The aqueous phase contains water.

The aqueous phase may also contain structuring agents such as carbomers or other thickeners, for example, xanthan gum, carageenan gum, polyacrylate-13; polyisobutene; polysorbate-20; polyacrylate-13/polyisobutylene/polysorbate-20 blends, and the like including mixtures thereof.

Preferably, the composition comprises a thickener and the thickener is hydroxyethyl acrylate/sodium acryloyldimethyl taurate copolymer.

The oil phase contains at least one cosmetically-acceptable oil.

As used herein, the term "oil" means a hydrophobic material that can aid in balancing the intermolecular forces to form micelle aggregates or to limit their sizes. Oils also serve as emollient ingredients to benefit product spreadibility, skin feel and delivery of hydrophobic active ingredients such as but not limited to, Vitamins D, E, K and A, and sunscreen filters.

Oils that are useful in the composition include a variety of hydrocarbon-based oils, silicones, fatty acid derivatives, glycerides, vegetable oils, vegetable oil derivatives, alkyl esters, wax esters, beeswax derivatives, sterols, and phospholipids and combinations thereof ranging from approximately 20% to 50%, based on the total weight of the composition.

Suitable hydrocarbon oils include petrolatum, mineral oil, micro-crystalline waxes, squalene and combinations thereof.

Silicone oils include dimethicone, dimethiconol, phenyl dimethicone and cyclic polysiloxanes and combinations thereof. Silicone oils having viscosities from about 0.5 to about 100,000 centistokes at 25° C. may also be useful in the composition.

Glycerides include castor oil, sunflower seed oil, coconut oil and derivatives, vegetable oils and derivatives, palm oil, jojoba oil, Shea butter, lanolin and combinations thereof.

Alkyl ester oils include, but are not limited to, isopropyl esters of fatty acids and esters of long chain fatty acids. More preferably, the following alkyl esters are useful: isopropyl palmitate, isopropyl myristate, myristyl myristate, isohexyl palmitate, decyl oleate, isononyl isononanoate and combinations thereof.

The non-ionic lipid phase comprises one or more non-ionic lipids, such as glyceryl monoesters having a fatty acid chain containing from about 3 to about 50 carbon atoms, and preferably from about 10 to about 18 carbon atoms; glyceryl diesters having a fatty acid chain containing from about 5 carbon atoms to about 25 carbon atoms, and preferably from about 10 carbon atoms to about 18 carbon atoms; alkoxylated alcohols; alkoxylated alkyl phenols; alkoxylated acids; alkoxylated amides; alkoxylated sugar derivatives; alkoxylated derivatives of natural oils or waxes; polyoxyethylene polyoxypropylene block copolymers; polyoxyethylene ether fatty acids having a fatty acid chain containing from about 10 carbon atoms to about 18 carbon atoms; steroids; fatty acid esters of alcohols where the fatty acid is straight or branched chain having from about 10 carbon atoms to about 20 carbon atoms and the alcohol is straight or branched chain having 1 to 10 carbon atoms; and mixtures thereof, wherein the alkoxylated lipids are alkoxylated with ethylene oxide or propylene oxide, with ethylene oxide being preferred.

Examples of suitable glyceryl monoesters include, but are not limited to, glyceryl caprate, glyceryl caprylate, glyceryl cocate, glyceryl erucate, glyceryl hydroxysterate, glyceryl isostearate, glyceryl lanolate, glyceryl laurate, glyceryl linolate, glyceryl myristate, glyceryl oleate, glyceryl PABA, glyceryl palmitate, glyceryl ricinoleate, glyceryl stearate, glyceryl thiglycolate, and mixtures thereof, with glyceryl laurate and glyceryl myristate being preferred.

Examples of suitable glyceryl diesters include, but are not limited to, glyceryl dilaurate, glyceryl dioleate, glyceryl dimyristate, glyceryl disterate, glyceryl sesuioleate, glyceryl stearate lactate, and mixtures thereof, with glyceryl dilaurate and glyceryl dimyristate being preferred.

Examples of suitable polyoxyethylene fatty ethers include, but are not limited to, polyoxyethylene cetyl/stearyl ether, polyoxyethylene cholesterol ether, polyoxyethylene laurate or dilaurate, polyoxyethylene stearate or distearate, polyoxyethylene lauryl or stearyl ether, and mixtures thereof, wherein the polyoxyethylene head group ranges from about 2 to about 100 groups. Preferred polyoxyethylene fatty ethers include polyoxyethylene stearyl ether, polyoxyethylene myristyl ether, and polyoxyethylene lauryl ether having from about 3 to about 10 oxyethylene units.

Examples of suitable steroids include, but are not limited to, cholesterol, betasitosterol, bisabolol, and mixtures thereof.

Examples of suitable fatty acid esters of alcohols include isopropyl myristate, aliphati-isopropyl n-butyrate, isopropyl n-hexanoate, isopropyl n-decanoate, isproppyl palmitate, octyidodecyl myristate.

Exemplary alkoxylated alcohols useful as the nonionic lipid in the compositions of the invention have the structure shown in Formula I below:

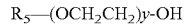

$$R_5-(OCH_2CH_2)y-OH \qquad \text{Formula I}$$

wherein $R_5$ is a branched or unbranched alkyl group having from about 6 to about 22 carbon atoms and y is between about 4 and about 100, and preferably, between about 10 and about 100. A preferred alkoxylated alcohol is the species wherein $R_5$ is a lauryl group and y has an average value of 23, which is known as laureth 23 and is available from ICI Americas, Inc. of Wilmington, Del. under the tradename "BRIJ 35."

Another exemplary alkoxylated alcohol is an ethoxylated derivative of lanolin alcohol. Lanolin alcohol is a mixture of organic alcohols obtained from the hydrolysis of lanolin. An example of an ethoxylated derivative of lanolin alcohol is laneth-10, which is the polyethylene glycol ether of lanolin alcohol with an average ethoxylation value of 10.

Another exemplary alkoxylated alcohol is polyoxypropylene polyoxyethylene alkyl ether, for example PPG-12-Buteth-16. This material is available from Amerchol Corp. of Edison, N.J. under the tradename, "UCON Fluid 50-HB-660."

Another type of non-ionic lipids includes alkoxylated alkyl phenols, for example nonoxynol-14" and is available under the tradename, "MAKON 14" from the Stepan Company of Northfield, Ill.

Another type of non-ionic lipids is alkoxylated acids, which are esters of an acid, most usually a fatty acid, with a polyalkylene glycol, for example PEG-8 laurate.

Another type of non-ionic lipids includes alkoxylated amides, for example PEG-6 cocoamide.

Another type of non-ionic lipids includes the alkoxylated sugar derivatives, for instance polysorbate 20, a mixture of laurate esters of sorbitol and sorbitol anhydrides, consisting predominately of the monoester, condensed with about 20 moles of ethylene oxide. This material is available under the tradename "TWEEN 20" from ICI Americas of Wilmington, Del.

Another example of an alkoxylated sugar derivative useful in the compositions of the invention is PEG-20 methylglucose sesquistearate, which is the polyethyleneglycol ether of the sesquiester of methyl glucose and stearic acid, contains an average of 20 moles of ethylene oxide, and is available under the tradename, "Glucamate SSE-20" from the Amerchol Corp. of Edison, N.J.

Another type of non-ionic lipids includes the alkoxylated derivatives of natural oils and waxes. Examples of this class of material include PEG-40 lanolin, PEG-40 castor oil and PEG-40 hydrogenated castor oil.

Another type of non-ionic lipids includes polyoxyethylene polyoxypropylene block copolymers, for example Poloxamer 101 and Poloxamer 182.

Preferred nonionic lipids include polyoxyethylene fatty ethers, glyceryl diesters, and mixtures thereof. More preferred nonionic lipids include polyoxyethylene stearyl ether, polyoxyethylene myristyl ether, and polyoxyethylene lauryl ether, glyceryl dilaurate, glyceryl dimystate, glyceryl distearate, and mixtures thereof, whereby each ether has from about 5 to about 10 oxyethylene units.

In an embodiment wherein the reduction of skin irritation is a concern, it is preferable to use a nonionic lipid having a greater amount of carbon atoms on the hydrophilic head group moiety, or in the alternative, a nonionic lipid having a greater amount of carbon atoms on the hydrophobic fatty acid chain moiety. The former can be achieved by increasing the amount of carbon atoms on the head group of, for example, a polyoxyethylene-10-stearyl ether from about 10 carbon atoms to from about 15 to 20 carbon atoms. The latter can be achieved by increasing the amount of carbon atoms on the 12 carbon fatty acid tail of, for example, glyceryl diesters to from about 14 carbons to about 16 carbons.

The composition of the present invention includes, based upon the total weight of the composition, from about 1 percent to about 10 percent, and preferably from about 3 percent to about 7 percent of the nonionic lipid.

In a preferred embodiment, the non-ionic lipid phase comprises water, glyceride dilaurate, steareth-10, and glycerin.

In one embodiment the composition comprises hyaluronic acid, lactic acid, steareth 10, glycerol dilaurate, and glycerin. The hyaluronic acid may be linear hyaluronic acid. The hyaluronic acid may be cross-linked hyaluronic acid. The hyaluronic acid may be a mixture of linear and cross-linked hyaluronic acid.

In another embodiment, the composition comprises lactic acid, steareth 10, glycerol dilaurate, and glycerin.

Topical Compositions

The compositions of the present invention are applied topically to human skin or hair. Accordingly, the composition may further include a cosmetically acceptable topical carrier that may be from about 50% to about 99.99%, by weight, of the composition (e.g., from about 80% to about 99%, by weight, of the composition). In a preferred embodiment of the invention, the cosmetically acceptable topical carrier includes water.

The compositions may be made into a wide variety of product types that include but are not limited to lotions, creams, gels, sticks, sprays, ointments, cleansing liquid washes and solid bars, shampoos and hair conditioners, hair fixers, pastes, foams, powders, mousses, shaving creams, wipes, patches, hydrogels, film-forming products, facial masks and skin masks, films and make-up such as foundations, and mascaras. These product types may contain several types of cosmetically acceptable topical carriers including, but not limited to, solutions, suspensions, emulsions such as microemulsions and nanoemulsions, gels, solids and liposomes. The following are non-limiting examples of such carriers. Other carriers can be formulated by those of ordinary skill in the art.

The compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include propylene glycol, polyethylene glycol, polypropylene glycol, glycerol, 1,2,4-butanetriol, sorbitol esters, 1,2,6-hexanetriol, ethanol, and mixtures thereof.

Compositions useful in the subject invention may be formulated as a solution comprising an emollient. Such compositions preferably contain from about 2% to about 50% of an emollient(s). As used herein, "emollients" refer to materials used for the prevention or relief of dryness, such as by preventing the transepidermal loss of water from the skin. Examples of emollients include, but are not limited to, those set forth in the *International Cosmetic Ingredient Dictionary and Handbook*, eds. Pepe, Wenninger and McEwen, pp. 2930-36 (The Cosmetic, Toiletry, and Fragrance Assoc., Washington, D.C., 9th Edition, 2002) (hereinafter "ICI Handbook"). Examples of particularly suitable emollients include vegetable oils, mineral oils, fatty esters, and the like.

A lotion can be made from such a solution. Lotions typically contain from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

The composition of the present invention may include water or alternatively be anhydrous or be an ointment that includes no water but organic and/or silicone solvents, oils, lipids and waxes. An ointment may contain a simple base of animal or vegetable oils or semi-solid hydrocarbons. An ointment may contain from about 2% to about 10% of an emollient(s) plus from about 0.1% to about 2% of a thickening agent(s). Examples of thickening agents include, but are not limited to, those set forth in the ICI Handbook pp. 2979-84.

The composition may be formulated as an emulsion. If the topical carrier is an emulsion, from about 1% to about 10% (e.g., from about 2% to about 5%) of the topical carrier contains an emulsifier(s). Emulsifiers may be nonionic, anionic or cationic. Examples of emulsifiers include, but are not limited to, those set forth in the ICI Handbook, pp. 2962-71.

Lotions and creams can be formulated as emulsions. Typically such lotions contain from 0.5% to about 5% of an emulsifier(s). Such creams typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, soap bar composition, powder, or a wipe containing powder).

The compositions useful in the subject invention may contain, in addition to the aforementioned components, a wide variety of additional oil-soluble materials and/or water-soluble materials conventionally used in compositions for use on skin and hair, at their art-established levels.

Additional Cosmetically Acceptable Active Agents

In one embodiment, the composition contains an additional cosmetically acceptable active agent.

In one embodiment, the additional agent is selected from, but not limited to, the group consisting of hydroxy acids, benzoyl peroxide, D-panthenol, octyl methoxycinnimate, octyl salicylate, homosalate, avobenzone, carotenoids, retinoids such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides including those containing copper, coenzyme Q10, amino acids such as proline, vitamins, lactobionic acid, acetyl-coenzyme A, niacin, riboflavin, thiamin, ribose, electron transporters such as NADH and FADH2, and other botanical extracts such as aloe vera, feverfew, oatmeal and derivatives and mixtures thereof. The additional cosmetically active agent will typically be present in the composition of the invention in an amount of from about 0.001% to about 20% by weight of the composition, e.g., about 0.005% to about 10% such as about 0.01% to about 5%.

Examples of vitamins include, but are not limited to, vitamin A, vitamin B's such as vitamin B3, vitamin B5, and vitamin B12, vitamin C, vitamin K, and different forms of vitamin E like alpha, beta, gamma or delta tocopherols or their mixtures, and derivatives thereof.

Examples of hydroxy acids include, but are not limited to, glycolic acid, lactic acid, malic acid, salicylic acid, citric acid, and tartaric acid.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but are not limited to, extracts containing flavonoids and isoflavonoids and their derivatives (e.g., genistein and diadzein), extracts containing resveratrol and the like. Examples of such natural extracts include grape seed, green tea, pine bark, and propolis.

Other Materials

Various other materials may also be present in the composition, as known in the art. These include humectants, pH adjusters, chelating agents (e.g., EDTA), fragrances, dyes, and preservatives (e.g., parabens).

The composition and formulations and products containing such compositions of the present invention may be prepared using methodology that is well known by an artisan of ordinary skill.

The composition provides increased topical delivery of the cosmetically acceptable active ingredient by increasing its penetration through the stratum corneum.

Method of Increasing Topical Delivery

In one embodiment, the invention provides a method of increasing the topical delivery of a cosmetically acceptable active ingredient having a pKa of about 2.8 to about 4, comprising topically administering the cosmetically acceptable active ingredient in a composition having a pH of about 3.3 to about 4, a buffer capacity of at least about 0.15, and containing a buffering agent having a pKa of about 2.8 to about 4.2.

As used herein, "topical delivery" of an active ingredient means 1) penetration of the active ingredient into human skin, or 2) retention of the active ingredient in human skin, or 3) both penetration into and retention of the active ingredient in human skin. Using the method of the invention, preferably both the penetration into and retention of a cosmetically acceptable active ingredient in human skin is increased.

For example, the topical delivery of a cosmetically acceptable active ingredient may be doubled or more compared with its topical delivery when contained in a composition having a pH of greater than 4 but otherwise the same.

Alternatively, the topical delivery of a cosmetically acceptable active ingredient may be doubled or more compared with its topical delivery when contained in a composition not containing the buffering agent having a pKa of about 2.8 to about 4.2 but otherwise the same.

In a preferred embodiment, the cosmetically acceptable active ingredient comprises hyaluronic acid. In particular, the hyaluronic acid may comprise linear hyaluronic acid, cross-linked hyaluronic acid, or a mixture of linear and hyaluronic acid hyaluronic acid. For example, the cosmetically acceptable active ingredient may comprise cross-linked hyaluronic acid For purposes of the method of the invention, penetration of hyaluronic acid is measured using the following Hyaluronic Acid Penetration Test, which measures biodelivery of hyaluronic acid. Human epidermal equivalent tissues (MatTek Corporation, EpiDerm-Epi-200) are used. The epidermal equivalent tissues are handled and cultured following the vendor's instructions. A 6 ul sample of a test composition is topically applied on a tissue, which is then maintained in culture in an incubator at 5% $CO_2$, 37° C. Culture media underneath the tissue is collected 24 hours post-treatment, and measured for HA presence using a Hyaluronan ELISA kit (Echelon, Inc., cat. #K-1200) following the manufacturer's instructions. To assess HA presence, the colorimetric change of the reagents is measured at 405 nm using a microplate reader (Versamax, Molecular Devices Inc.).

The following non-limiting examples further illustrate the invention.

Example 1

A series of inventive and comparative compositions were made using the ingredients shown in Table 1. The inventive and comparative compositions all consisted of three phases: a main, aqueous phase, an oil phase, and a non-ionic lipid phase. The compositions were prepared using the following procedure while varying the quantities of lactic acid (buffering agent) and sodium lactate (pH adjuster) as discussed in the Examples that follow.

TABLE 1

| Ingredient | Trade Name | INCI Name | % wt |
|---|---|---|---|
| 1 | Purified water | Water | QS to 100 |
| 2 | Sepimax C | Hydroxyethyl Acrylate/Sodium Acryloyldimethyl Taurate Copolymer | 0.90 |
| 3 | USP Grade Kosher Glycerin | Glycerin | 2.00 |
| 4 | Versene NA Chelating Agent | Disodium EDTA | 0.10 |
| 5 | Cosvat | Chlorphensin | 0.20 |
| 6 | Finsolv TN | C12-15 Alkyl Benzoate | 2.25 |
| 7 | Crodacol C-95-PA-(MH) | Cetyl Alcohol | 2.50 |
| 8 | Lanette 18 | Stearyl Alcohol | 2.00 |
| 9 | Arlacel 165-PW-(AP) CB46951 | Glyceryl Stearate; PEG-100 Stearate | 4.00 |
| 10 | Triple Pressed Stearic Acid (Pofac 1655L) | Stearic Acid | 0.40 |
| 11 | Palmitic Acid, 98% FGK, Flakes | Palmitic Acid | 0.40 |
| 12 | Xiameter PMX-200 Silicone 50 cs | Dimethicone | 0.25 |
| 13 | Akoline SL | Sodium Stearoyl Lactate | 0.25 |
| 14 | Cithrol PGMIS-LQ-GD (ESG2034) | Propylene Glycol Isostearate | 0.75 |
| 15 | Ceraphyl 28 | Cetyl Lactate | 0.50 |
| 16 | Ceraphyl 41 | C12-15 Alkyl Lactate | 1.00 |
| 17 | Purified Water | Water | 9.00 |
| 18 | USP Grade Kosher Glycerin | Glycerin | 1.00 |
| 19 | Emulsynt GDL | Glyceryl Dilaurate | 0.50 |
| 20 | BRIJ S10-SO (AP) (ET47454) | Steareth-10 | 0.50 |
| 21 | Hyacare Filler CL | Water; Ethylhexyl Stearate; Sodium Hyaluronate Crosspolymer; Polyglyceryl-4 Diisostearate/Polyhydroxystearate/Sebacate; Sodium Isostearate; Ethanol | 2.50 |
| 22 | Propylene Glycol USP/EP | Propylene Glycol | 3.00 |
| 23 | Arlasilk PTC-LQ-(AP) | Cocamidopropyl PG-Dimonium Chloride Phosphate | 1.00 |
| 24 | Euxyl PE 9010 | Phenoxyethanol; Ethylhexylglycerin | 0.80 |
| 25 | Ritalac LA (Lactic Acid USP) | Lactic Acid | Varies |
| 26 | Youthful Skin MOD2 4914/2 | Fragrance | 0.30 |
| 27 | Purasal S/HQ 60 | Sodium Lactate; Water | As needed to reach desired pH |

To make the main phase (ingredients 1-5 in Table 1) of each composition, a mixing vessel was charged with purified water and mixing was started. The thickener or viscosity-increasing agent (Sepimax C) was added to the vessel and mixed in until fully dispersed. Once dispersed, the main phase was heated to 75-80° C. While heating, the chelating agent (disodium EDTA), moisturizer/humectant (glycerin) and preservative (chlorphenesin) were added. The main phase was held at 75-80° C. with continuous mixing until the phasing step below.

To make the oil phase (ingredients 6-16 in Table 1), a side vessel was charged with emulsifiers/emulsion stabilizers (stearic acid, palmitic acid, sodium stearoyl lactylate, glyceryl stearate, PEG-100 stearate, stearyl alcohol, and cetyl alcohol), which were mixed and heated to 75-80° C. Emollients/skin conditioners (C12-15 alkyl benzoate, dimethicone, propylene glycol isostearate, C12-15 alkyl lactate, and cetyl lactate) were then added to the vessel and mixed until a uniform solution was obtained at a temperature of 75-80° C. The heating was continued until the temperature reached 80-85° C., at which time the oil phase was held for the phasing step described below.

To make the non-ionic lipid phase (ingredients 17-20 in Table 1), a vessel was charged with purified water and mixed on high, and heated to 60-65° C. while mixing in the non-ionic lipid ingredients (glyceride dilaurate, POE—steareth-10 and glycerin) until uniform, then held at 60-65° C. until addition to main phase.

To complete the phasing step, the main phase (75-80° C.) and oil phase (75-80° C.) were combined by adding the oil phase to the main phase. The temperature was maintained at 75-80° C. and the mixture was agitated until uniform. Once the phases were uniform, the vessel was cooled to 55-60° C., at which time Hyacare Filler CL (cross linked hyaluronic acid (HA)) was added to the vessel and mixed until ingredients became fully dispersed and uniform throughout the batch. The batch was further cooled to 50-55° C. and the non-ionic lipid phase was added to the batch. The batch was then mixed until all ingredients were fully dispersed and uniform. Once uniform, the batch was cooled to 35-40° C., and the buffering agent (lactic acid), preservative (phenoxyethanol; ethylhexylglycerin), propylene glycol, and fragrance were added. The batch was mixed until uniform. pH was adjusted slowly to the desired range using sodium lactate.

Example 2

Six compositions, 2A-2F were made as described in Example 1, and tested for hyaluronic acid (HA) penetration using the Hyaluronic Acid Penetration Test described above. The compositions were made without lactic acid and varying pH's. All of the compositions had buffer capacities of less than 0.002.

The results are shown in Table 2. The greatest percent increase in HA penetration over the untreated sample was only 64% (Composition 2D).

TABLE 2

| Composition | pH | Lactic Acid (wt %) | Buffer capacity | HA Penetration (ng/ml) |
|---|---|---|---|---|
| 2A | 3.0 | 0 | Less than 0.002 | 93 |
| 2B | 3.3 | 0 | Less than 0.002 | 75 |
| 2C | 4.0 | 0 | Less than 0.002 | 82 |
| 2D | 4.5 | 0 | Less than 0.002 | 113 |
| 2E | 5.0 | 0 | Less than 0.002 | 77 |
| 2F | 6.0 | 0 | Less than 0.002 | 106 |
| Untreated | — | — | — | 69 |

Example 3

Four compositions were made as described in Example 1, and tested for hyaluronic acid (HA) penetration using the Hyaluronic Acid Penetration Test. The compositions had a fixed pH of 3.3, but different amounts of lactic acid and different buffer capacities.

The results are shown in Table 3. There was a clear, direct dependence of HA penetration on buffer capacity. Compositions 3A and 3B, having buffer capacities of less than 0.1, showed increases in HA penetration of 10% and 119%, respectively. However, Compositions 3C and 3D according to the invention and having buffer capacities greater than 0.1 showed HA penetration four and five times, respectively, greater than the untreated sample, and more than double that achieved with the Compositions 3A and 3B.

TABLE 3

| Composition | pH | Lactic Acid (wt %) | Buffer capacity | HA Penetration (ng/ml) |
|---|---|---|---|---|
| 3A | 3.3 | 0 | Less than 0.002 | 76 |
| 3B | 3.3 | 1 | 0.044 | 151 |
| 3C | 3.3 | 3 | 0.13 | 348 |
| 3D | 3.3 | 6 | 0.26 | 467 |
| Untreated | — | — | — | 69 |

Example 4

Six compositions made according to Example 1 were tested for hyaluronic acid (HA) penetration using the Hyaluronic Acid Penetration Test. The compositions each contained 6 wt % lactic acid, but had pH's ranging from 3.0 to 6.0 and buffer capacities of 0.01 to 0.37.

The results are shown in Table 4. There was a clear inverse relationship between HA penetration and pH.

TABLE 4

| Composition | pH | Lactic Acid (wt %) | Buffer capacity | HA Penetration (ng/ml) |
|---|---|---|---|---|
| 4A | 3.0 | 6.0 | 0.17 | 634 |
| 4B | 3.3 | 6.0 | 0.26 | 467 |
| 4C | 4.0 | 6.0 | 0.37 | 299 |
| 4D | 4.5 | 6.0 | 0.23 | 107 |
| 4E | 5.0 | 6.0 | 0.09 | 69 |
| 4F | 6.0 | 6.0 | 0.01 | 113 |
| Untreated | — | — | — | 69 |

Example 5

Four compositions made according to Example 1 were tested for hyaluronic acid (HA) penetration using the Hyaluronic Acid Penetration Test. The compositions contained varying amounts of lactic acid, with buffer capacities of less than 0.002 to 0.021. Each composition had a pH of 6.

The results are shown in Table 5. None of these compositions increased the hyaluronic acid penetration by more than 18% (Composition 5D) over the untreated sample.

TABLE 5

| Composition | pH | Lactic Acid (wt %) | Buffer capacity | HA Penetration (ng/ml) |
|---|---|---|---|---|
| 5A | 6.0 | 0.0 | Less than 0.002 | 500.2 |
| 5B | 6.0 | 6.0 | 0.011 | 379 |
| 5C | 6.0 | 10.0 | 0.018 | 283 |
| 5D | 6.0 | 12.0 | 0.021 | 512 |
| Untreated | — | — | — | 433 |

Example 6

This example demonstrates that other buffering agents may be used according to the invention.

Four compositions were made according to Example 1 using glycolic acid instead of lactic acid as the buffering agent. They were tested for hyaluronic acid (HA) penetration using the Hyaluronic Acid Penetration Test. Compositions 6A, 6B, and 6C had a pH of 3.3. The amount of glycolic acid and buffer capacities varied.

The results are shown in Table 6. HA penetration was dependent on the amount of glycolic acid.

Composition 6D was made with 6% glycolic acid and a pH of 6.0 (buffer capacity 0.01), which showed only a 14% increase in HA penetration over the untreated sample.

TABLE 6

| Composition | pH | Buffer agent, wt % | Buffer capacity | HA Penetration (ng/ml) |
|---|---|---|---|---|
| 6A | 3.3 | Glycolic Acid, 1.0% | 0.05 | 797 |
| 6B | 3.3 | Glycolic Acid, 3.0% | 0.16 | 1544 |
| 6C | 3.3 | Glycolic Acid, 6.0% | 0.32 | 2131 |
| 6D | 6.0 | Glycolic Acid, 6.0% | 0.01 | 494 |
| Untreated | — | — | — | 433 |

Example 7

The effects on skin pH were tested using compositions 3B and 3D. Each composition was applied to the forearm of three human volunteers along with a non-buffered control formulation otherwise the same but containing no lactic acid. Both test compositions had a pH of 3.3.

Skin pH was measured before application and four hours following application using a Skin pH Meter 905 (Courage and Khazaka).

After four hours, skin pH was reduced by 0.593 pH units for Composition 3B, but 1.28 pH units for the buffered formulation Composition 3D, indicating a higher ability of the buffered formula to overcome the skin's own buffering system. The difference represents about 5 fold greater level of skin acidity, as measured by H+ ions, for the buffered vs the nonbuffered control.

This data demonstrates the utility and advantage of a composition according to the invention for maintaining a low skin pH over time.

Example 8

A series of compositions according to the invention were made using the ingredients in Table 7. The various thickeners shown in Table 8 below were substituted into the compositions.

TABLE 7

| Ingredient | Trade Name | INCI name | Concentration % |
|---|---|---|---|
| 1. | Purified water | Water | QS to 100 |
| 2. | | Thickener from TABLE 8 | Varies |
| 3. | USP Grade Kosher Glycerin | Glycerin | 2 |
| 4. | Versene NA Chelating agent | Disodium EDTA | 0.1 |
| 5. | Cosvat | Chlorphenesin | 0.2 |
| 6. | Finsolv TN | C12-15 Alkyl Benzoate | 2.25 |
| 7. | Crodacol C-95-PA-(MH) | Cetyl alcohol | 2.5 |
| 8. | Lanette 18 | Stearyl alcohol | 2 |
| 9. | Arlacel 165-PW-(AP) CB46951 | Glyceryl stearate; PEG-100 stearate | 4 |
| 10. | Triple pressed Stearic acid (Profac 1655L) | Stearic acid | 0.4 |
| 11. | Palmitic acid, 95% FGK, Flakes | Palmitic acid | 0.4 |
| 12. | Xiameter PMX-200 Silicone Fluid 50 cs | Dimethicone | 0.25 |
| 13. | Akoline SL | Sodium Stearoyl Lactylate | 0.25 |
| 14. | Cithrol PGMIS-LQ-GD (ESG2034) | Propylene Glycol Isostearate | 0.75 |
| 15. | Ceraphyl 28 | Cetyl lactate | 0.5 |
| 16. | Ceraphyl 41 | C12-15 Alkyl Lactate | 1 |
| 17. | Frescolat ML (620105) | Menthyl lactate | 0.9 |
| 18. | Purified Water | Water | 9 |
| 19. | USP Grade Kosher Glycerin | Glycerin | 1 |
| 20. | Emulsynt GDL | Glyceryl Dilaurate | 0.5 |
| 21. | Brij S10-SO (AP) (ET47454) | Steareth-10 | 0.5 |
| 22. | Hyacare Filler CL | Water; Ethylhexyl Stearate; Sodium Hyaluronate Crosspolymer; Polyglyceryl-4 Diisostearate/Polyhydroxystearate/Sebacate; Sodium Isostearate; Ethanol | 10 |
| 23. | Propylene Glycol USP/EP | Propylene glycol | 3 |
| 24. | Arlasilk PTC-LQ-(AP) | Cocamidopropyl PG-Dimonium Chloride Phosphate | 1 |
| 25. | Euxyl PE 9010 | Phenoxyethanol; Ethylhexylglycerin | 0.8 |
| 26. | Ritalac LA (Lactic acid USP) | Lactic acid | 5.7 |
| 27. | Purasal S/HQ 60 | Sodium Lactate | As needed to reach desired pH |

Six formulations were made using the above base formula, and substituting various thickeners as described in Table 8, which also shows the HA penetration levels.

TABLE 8

| Thickener | Description | pH of the composition | HA Penetration (ng/ml) |
|---|---|---|---|
| 1. | 0.6% Magnesium Aluminum Silicate (Veegum) | 3.3 | 803 |
| 2. | 0.9% Hydroxyethyl Acrylate/Sodium Acryloyldimethyl Taurate Copolymer (Sepimax C) | 3.3 | 541 |
| 3. | 0.4% Xanthan gum | 3.3 | 1302 |
| 4. | 3% Silica (Aerosil 200) | 3.3 | 239 |
| 5. | 0.6% Cetyl Hydroxyethylcellulose (Natrosol Plus 330) | 3.3 | 439 |
| 6. | x1.5% Polyacrylate-13; Polyisobutene; Polysorbate-20 (Sepiplus 400) - This formulation was also made without propylene glycol and propylene glycol isostearate. | 3.3 | 1188 |
| 7. | Untreated | NA | 94.6 |

All six formulations were low pH formulas with buffer capacities of 0.26. All the formulations delivered HA into the skin; however, formulation 4 only modestly delivered HA. Formulation 2 provided good HA delivery into the skin as well as good aesthetics.

Example 9

A daily wear composition according to the invention containing sun filters was made using the ingredients shown in Table 9 by the process described below.

TABLE 9

| Ingredient | Trade Name | INCI name | Concentration % |
|---|---|---|---|
| 1 | Purified Water | Water | QS to 100 |
| 2 | Ritalac LA (Lactic acid USP) | Lactic acid | 5.7 |
| 3 | Granulated Amigel | Sclerotium gum | 0.5 |
| 4 | Glycerin 99% USP | Glycerin | 2 |
| 5 | Xantural 180 | Xanthan gum | 0.4 |
| 6 | Versene NA chelating agent | Disodium EDTA | 0.1 |
| 7 | Cosvat | Chlorphenesin | 0.2 |
| 8 | Lex gard O | Caprylyl Glycol | 0.6 |
| 9 | D-Panthenol, USP | Panthenol | 0.2 |
| 10 | Crodamol PMP-LQ-(MH) ES43395 | PPG-2 Myristyl Ether Propionate | 5 |
| 11 | Finsolv TN | C12-15 Alkyl Benzoate | 5 |
| 12 | Neo Heliopan OS/BP (182562) | Octisalate | 5 |
| 13 | Uvinul N 539 T | Octocrylene | 3 |
| 14 | Neo Heliopan BB (116210) (US Sunscreen ACTIVE) | Oxybenzone | 4 |
| 15 | Triple Pressed Steaic acid (Profac 1655L) | Stearic acid | 2 |
| 16 | Arlacel 165-PW-(AP) CB46951 | Glyceryl stearate; PEG-100 Stearate | 3 |
| 17 | CO-1695 | Cetyl alcohol | 2 |
| 18 | Neo Heliopan 357 (US Sunscreen Active) | Avobenzone | 1.5 |
| 19 | Hyacare Filler CL | Water; Ethylhexyl Stearate; Sodium Hyaluronate Crosspolymer; Polyglyceryl-4 Diisostearate/Polyhydroxystearate/Sebacate; Sodium Isostearate; Ethanol | 10 |
| 20 | Purified Water | Water | 9 |
| 21 | Glycerin 99% USP | Glycerin | 1 |
| 22 | Emulsynt GDL | Glyceryl Dilaurate | 0.5 |
| 23 | Brij S10-SO (AP) (ET47454) | Steareth-10 (BRIJ 10) | 0.5 |
| 24 | dl-Alpha Tocopheryl Acetate 04 20085 | Tocopheryl Acetate | 0.5 |
| 25 | Tristat P25/ Phenoxyethanol P25 | Phenoxyethanol | 0.6 |
| 26 | Purasal S/HQ 60 | Sodium Lactate; Water | As needed to reach desired pH |

First, xanthan gum and glycerin were mixed in a side container.

Next, a non-ionic lipid phase (ingredients 20-23) was made by mixing 9% water, glycerin, glyceryl dilaurate, and steareth 10 in a mixing vessel, mixed on high, and heated to 65° C.

Then to make the oil phase (ingredients 10-18), stearic acid, glyceryl stearate, PEG-100 stearate, cetyl alcohol, octisalate, Finsolv TN, Crodamol PMP, avobenzone, octocrylene, and oxybenzone were added to a mixing vessel, and heated to 75-80° C. while mixing. The temperature was maintained until ready for emusification.

To make the main phase (ingredients 1-3), water and lactic acid were slowly added to a mixing vessel and mixed on high. *Sclerotium* gum was sprinkled in. After a uniform mixture was achieved, the xanthan gum phase was added. The contents of the vessel were mixed until uniform, then heated to 75-80° C., at which time disodium EDTA, chlorphenesin, Lexgard O and panthenol were added. The temperature was maintained at 75-80° C. for five minutes.

Emulsification was performed at 75-80° C. by first adding the oil phase to the main phase and mixing for five minutes, then cooling. While cooling, Hyacare Filler was added at 60° C. The non-ionic lipid phase was added at 50° C. Tocopheryl acetate and phenoxyethanol were added at 40° C., and the resulting mixture was mixed until uniform. The batch was then cooled to 35 C.

The pH of the composition was adjusted to 3.3 with sodium lactate, and QS to 100% with purified water.

The composition was tested for HA penetration using the Hyaluronic Acid Penetration Test, showing strong biodelivery of HA (863 ng/ml) compared to untreated (69 ng/ml).

Example 10

Two daily wear compositions were made according to Example 9, except one contained 0% lactic acid with buffer capacity of <0.001 (comparative composition 11A), and the other contained 6% lactic acid with buffer capacity of 0.26 (inventive composition 11B). The pH of each composition was 3.3.

The compositions were topically applied to human epidermal equivalent tissues (MatTek Corporation, EpiDerm-Epi-200) as described in connection with the Hyaluronic Acid Penetration Test. Culture media underneath each tissue were collected at 1 h, 6 h and 24 h post-treatment. The collected culture media were fixed in an acid-formalin solution. After fixation for 24 hours in the acid-formalin solution, the tissues were dehydrated and impregnated in paraffin. 5-µm-thick paraffin sections were realized, and the sections were then mounted on Superfrost® plus silanized glass slides. Hyaluronic acid immuno-staining was performed on the paraffinized sections with an anti-biotinylated hyaluronic acid (HABP) (EMD Millipore) and amplified with a biotin/streptavidin system (Vector Laboratories) and revealed in blue color. The staining was assessed by microscopic observation with a Leitz microscope using a Leica DFC 320 camera and Image Pro Plus software (Media Cybernetics). To assess HA penetration, the intensity of exogenous HA revealed in blue color was quantified using Adobe Photoshop CS5 software (Adobe Systems Inc.). The data was expressed as relative to a 256 color scale.

Tissue treated with inventive composition 11B at the 1 h time-point post-treatment showed HA remaining above the tissue, and there was an absence of penetrated HA in the superficial layers within the tissues. However, at 6 h and 24 h post-treatment, the HA had completely penetrated inside the tissue as revealed by the blue staining of the upper layers within the tissues, and disappearance of blue stain above the tissues.

In contrast, tissue treated with the comparative composition 11A showed HA stain above the tissue and an absence of penetrated HA in the superficial layers within the tissues at all time points.

The results are shown in Table 10.

TABLE 10

| | Time | HA Penetration (ng/ml) | Un-penetrated HA above the tissue (Relative Intensity Units) | Penetrated HA inside the tissue (Relative Intensity Units) |
|---|---|---|---|---|
| Untreated | 1 h | 273 | 16 | 26 |
| | 6 h | 270 | 15 | 25 |
| | 24 h | 415 | 15 | 25 |
| Inventive composition 11B | 1 h | 425 | 70 | 30 |
| | 6 h | 1873 | 22 | 35 |
| | 24 h | 5381 | 22 | 29 |
| Comparative composition 11A | 1 h | 262 | 76 | 27 |
| | 6 h | 323 | 71 | 27 |
| | 24 h | 626 | 58 | 26 |

This Example shows that compositions according to the invention advantageously provide both penetration into and retention in tissue.

The invention claimed is:

1. A topical composition comprising:
   (a) about 3 to about 6 wt % of a buffering agent having a pKa of about 2.8 to about 4.2; and
   (b) a cosmetically acceptable active ingredient comprising a glycosaminoglycan and having a pKa within about 1 unit of the pKa of the buffering agent;
wherein the composition has a pH of 3.3 to 4 and a buffer capacity of at least about 0.15.

2. The topical composition of claim 1, wherein the cosmetically acceptable active ingredient has a pKa within about 0.7 unit of the pKa of the buffering agent.

3. The topical composition of claim 1, wherein the cosmetically acceptable active ingredient comprises hyaluronic acid.

4. The topical composition of claim 1, wherein the cosmetically acceptable active ingredient comprises cross-linked hyaluronic acid.

5. The topical composition of claim 1, wherein the buffering agent is selected from the group consisting of lactic acid, glycolic acid, citric acid, tartaric acid, gluconic acid, and gluconolactone.

6. The topical composition of claim 1, wherein the buffering agent is lactic acid.

7. A topical composition comprising:
   (a) hyaluronic acid;
   (b) about 3 to about 6 wt % of lactic acid;
   (c) steareth 10;
   (d) glycerol dilaurate; and
   (e) glycerin;
wherein the composition has a pH of 3.3 to 4 and a buffer capacity of at least about 0.15.

8. The topical composition of claim 7, wherein the hyaluronic acid comprises cross-linked hyaluronic acid.

9. The topical composition of claim 7, further comprising a thickener selected from the group consisting of magnesium aluminum silicate, hydroxyethyl acrylate/sodium acryloyldimethyl taurate copolymer, xanthan gum, silica, cetyl hydroxyethylcellulose, and polyacrylate-13/polyisobutylene/polysorbate-20 blend, and mixtures thereof.

10. The topical composition of claim 9, wherein the thickener comprises hydroxyethyl acrylate/sodium acryloyldimethyl taurate copolymer.

11. A method of increasing the topical delivery of a cosmetically acceptable active ingredient having a pKa of about 2.8 to about 4, comprising topically administering the cosmetically acceptable active ingredient in a composition having a pH of 3.3 to 4, a buffer capacity of at least about 0.15, and containing about 3 to about 6 wt % of a buffering agent having a pKa of about 2.8 to about 4.2.

12. The method of claim 11, wherein said topical delivery is at least doubled compared with the topical delivery of the cosmetically acceptable active ingredient when contained in the composition having a pH of greater than 4.

13. The method of claim 11, wherein said topical delivery is at least doubled compared with the topical delivery of the cosmetically acceptable active ingredient when contained in the composition not containing said buffering agent.

14. The method of claim 11, wherein the cosmetically acceptable active ingredient comprises hyaluronic acid.

15. The method of claim 11, wherein the cosmetically acceptable active ingredient comprises cross-linked hyaluronic acid.

16. A topical composition comprising:
   (a) about 3 to about 6 wt % of lactic acid;
   (b) steareth 10;

(c) glycerol dilaurate; and
(d) glycerin;
wherein the composition has a pH of 3.3 to 4 and a buffer capacity of at least about 0.15.

17. The topical composition of claim 16, further comprising a thickener selected from the group consisting of magnesium aluminum silicate, hydroxyethyl acrylate/sodium acryloyldimethyl taurate copolymer, xanthan gum, silica, cetyl hydroxyethylcellulose, and polyacrylate-13/polyisobutylene/polysorbate-20 blend, and mixtures thereof.

18. The topical composition of claim 17, wherein the thickener comprises hydroxyethyl acrylate/sodium acryloyldimethyl taurate copolymer.

* * * * *